(12) United States Patent
Sherik et al.

(10) Patent No.: US 10,119,948 B2
(45) Date of Patent: Nov. 6, 2018

(54) SULFUR SOLUBILITY IN GAS MEASUREMENT SYSTEM

(71) Applicant: Saudi Arabian Oil Company, Dhahran (SA)

(72) Inventors: Abdelmounam Sherik, Dhahran (SA); Abderrazak Traidia, Abqaiq (SA); AbdulJalil Rasheed, Dammam (SA); Arnold Lewis, Fresno, TX (US)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 197 days.

(21) Appl. No.: 14/989,660

(22) Filed: Jan. 6, 2016

(65) Prior Publication Data

US 2017/0191972 A1    Jul. 6, 2017

(51) Int. Cl.
| | |
|---|---|
| G01N 33/00 | (2006.01) |
| G01G 19/00 | (2006.01) |
| C10L 3/10 | (2006.01) |
| G01N 33/22 | (2006.01) |
| G01N 25/14 | (2006.01) |

(52) U.S. Cl.
CPC .......... *G01N 33/0036* (2013.01); *C10L 3/103* (2013.01); *G01G 19/00* (2013.01); *G01N 33/225* (2013.01); *G01N 25/14* (2013.01)

(58) Field of Classification Search
CPC .. G01N 33/0036; G01N 25/14; G01N 33/225; G01N 33/00; C10L 3/103; G01G 19/00
See application file for complete search history.

(56) References Cited

U.S. PATENT DOCUMENTS

| | | | |
|---|---|---|---|
| 6,946,111 B2 | 9/2005 | Keller et al. | |
| 7,531,135 B2 | 5/2009 | D Haene et al. | |
| 8,084,263 B2 | 12/2011 | Al-taie et al. | |
| 2010/0240135 A1 | 9/2010 | Seeger et al. | |

OTHER PUBLICATIONS

Fadairo Adesina et al., "Elemental Sulphur Induced Formation Damage Management in Gas Reservoir", SPE 154980 presented at the SPE International Conference and Exhbition on Oilfield Scale held in Aberdeen, UK, May 30-31, 2012.*
Pack, David J., "'Elemental Sulphur' Formation in Natural Gas Transmission Pipelines", 2005, Doctoral Thesis.*

(Continued)

*Primary Examiner* — Lisa Caputo
*Assistant Examiner* — Irving A Campbell
(74) *Attorney, Agent, or Firm* — Leason Ellis LLP (57) ABSTRACT

This present disclosure is directed to a method and apparatus for collecting small amounts, sub mg levels, of elemental sulfur (or other trace elements such as mercury) deposited from the ppm levels of elemental sulfur (or other trace elements such as mercury) contained in gases found in typical oil production environments or gas streams with anticipated sulfur deposition problems, as well as in industries other than oil and gas. An analytical chemistry technique for determining the amount of sulfur collected is used and from this result, the solubility of sulfur in a gas at a fixed temperature, pressure and gas composition can be calculated.

24 Claims, 1 Drawing Sheet

(56) References Cited

OTHER PUBLICATIONS

Brunner, E. et al., "Solubility of Sulfur in Hydrogen Sulfide and Sour Gases," Society of Petroleum Engineers Journal, vol. 20, No. 5, p. 377-384, Oct. 1980.
Sun, C.Y. et. al., "Experimental and modeling studies on sulfur solubility in sour gas," Fluid Phase Equilibria, vol. 214, No. 2, pp. 187-195.
JP. Serin, P. Cézac, F. Broto, G. Mouton, "Modeling solubility of solid sulfur in natural gas"—Chemical Engineering Journal, Accepted Feb. 21, 2007.
Cézac P., Serin J.P., Reneaume J.M., Mercadier J. and Mouton G., 2008, Elemental Sulphur deposition in natural gas transmission and distribution networks, The Journal of Supercritical Fluids, 4, 2, 155-122. Accepted Nov. 9, 2007.

\* cited by examiner

SULFUR SOLUBILITY IN GAS MEASUREMENT SYSTEM

TECHNICAL FIELD

This present disclosure is directed to a method and apparatus for collecting small amounts, sub mg levels, of elemental sulfur (or other trace elements such as mercury) deposited from the ppm levels of elemental sulfur (or other trace elements such as mercury) contained in gases found in typical oil production environments or gas streams with anticipated sulfur deposition problems, as well as in industries other than oil and gas. A suitable analytical chemistry technique for determining the amount of sulfur collected is used and from this result, the solubility of sulfur in a gas at a fixed temperature, pressure and gas composition can be calculated.

BACKGROUND

The management of sulfur continues to be a persistent problem for sour gas and natural gas operations. In many sour gas operations, elemental sulfur vapor in the gas can condense and deposit at various locations along the sour gas system causing numerous problems. For example, sulfur depositions in gas pipelines and processing facilities can increase the rate of corrosion in the pipes and cause leaks or blockages that interrupt normal operation of the gas lines. Subsequent removal and disposal of the sulfur deposits can then cause safety and environmental concerns. Due to the problems associated with removing sulfur deposits, there is a need for ways to accurately predict the location of future sulfur deposits within the structures of a gas line (e.g., pipeline, pressure vessels, etc.) and also to predict the maximum amount of sulfur that can deposit.

Oil and gas production technical professionals are generally well aware of the fact that elemental sulfur is often found, either saturated or at significant levels, in reservoir gases. They are also generally aware of the fact that pressure or temperature reduction of the gas can result in precipitation and deposition of sulfur from the gas. Alternatively, what is very difficult for them to know are the locations in their facilities where they might expect to find deposited sulfur and at those locations, how much sulfur might be expected to deposit. Because of this lack of knowledge, oil and gas production engineers have a difficulty determining how to manage potential sulfur deposition in their facilities and the subsequent problems it can create. What is needed, and what is lacking in current art, is a sulfur deposition prediction model developed for use by oil and gas production personnel. To create such a model, tailored for oilfield gas operations, three types of data are required:

1. The amount of sulfur dissolved in a gas where it enters gas handling facilities, which is a function of its composition, pressure, and temperature
2. The amount of sulfur dissolved in the gas as a function of temperature reduction
3. The amount of sulfur dissolved in the gas as a function of pressure reduction Using current art, it is difficult to determine the quantity of sulfur in a gas stream where it enters a gas facility. However, it is not cost-effective or particularly feasible with current art, to determine the amount of sulfur dissolved in the gas as a function of temperature or pressure reduction. The following paragraphs explain this in detail.

More specifically, in the current art, there are laboratory-based techniques available, which attempt to provide the means for the accurate determination of sulfur in a gas. All of the current art laboratory-based techniques utilize a closed system in which a volume of gas is pressurized to a required pressure inside of a fixed volume equilibrium cell or autoclave that is controlled at a required temperature. Although fully capable of simulating any oilfield gaseous environment, a closed system of fixed volume is incapable of providing the means for the accurate determination of sulfur in the gas. The deficiency with the current art, laboratory-based techniques, results directly from the closed system of fixed volume. An example and discussion will clarify this point.

For this example, it will be assumed that researchers seek to create a sulfur deposition prediction model for a 100% methane gas stream found in typical oil and gas production environments. Therefore, accurate determinations of elemental sulfur in methane gas at pressures and temperatures typically found in gas production facilities will be required to create the model. One set of conditions, typical in gas production facilities containing methane, is one in which the methane is at 300-psia pressure and at 45° C. temperature. To conduct their testing, the research staff will use a typical current art, closed, fixed volume, autoclave vessel. To their benefit, the research staff recognizes that the larger the volume of their vessel the more improved will be their test results. They therefore decide to use a very large fixed volume vessel of 10-liters volume. Under the conditions of 300-psia pressure and 45° C. temperature, methane gas could typically contain 0.01-pounds of elemental sulfur per million standard cubic feet of gas. Current art analytical chemistry techniques require a minimum of approximately 0.1-milligram of deposited elemental sulfur for accurate and precise determinations. Therefore, under these conditions of pressure and temperature, the volume of methane gas required to collect 0.1-milligram of elemental sulfur, would be approximately 625 liters at standard 1-atmosphere pressure. At 300-psia pressure, this is approximately 31 liters of gas. Considering that the test vessel is 10-liters in volume, it is readily apparent that it will be impossible to remove 31 liters of gas from a 10-liter vessel in order to meet the requirements of the analytical technique. This makes it impossible for the research staff in this example to develop a sulfur deposition prediction model for methane gas found in typical oil and gas production environments. It could be argued that a larger autoclave vessel could have been used. This might be true, but the cost and complexity of using larger pressure vessels increases at a staggering rate. However, there is another subtle point that will show the deficiency of current laboratory art. To determine, accurately and precisely, the amount of sulfur in a gas, a sufficient volume of the gas must be sampled in order to collect adequate sulfur for the analytical chemistry analysis. In the above example, this was approximately 31 liters. Regardless whether the volume of sampled gas is one milliliter or 31 liters, it does represent the physical removal of gas from the fixed volume vessel. If one milliliter of gas is removed from a fixed volume vessel, then there will be less gas occupying the same volume and the pressure inside of the vessel must decrease. It is established that the saturation level of elemental sulfur contained in a gas is directly proportional to the pressure of the gas. Therefore, as gas is removed from a current art fixed volume vessel, the pressure inside the vessel will drop, and so will the amount of sulfur contained in the gas. This problem cannot be overcome by current art laboratory-based fixed volume vessels.

It will be appreciated that the foregoing example is exemplary in nature and is presented for illustrating the deficiencies of conventional techniques.

Also in the art, there are field-capable techniques available to oil and gas production engineers, which feasibly can provide the means for the accurate determination of sulfur in a gas. In this situation of field-based testing, potentially accurate results can be obtained because of the large volume of gas normally available, which overcomes the limitation of lab-based measurements described above. However, these methods are not commonly used because by itself, knowing the amount of sulfur in a gas at one particular location provides the engineer with very limited knowledge. The engineer would not know the amount of sulfur in the gas upstream from the measurement location and would have no ability to predict if, or how much, sulfur might precipitate and deposit in facilities downstream from the measurement location. In theory, engineering staff could determine the amount of sulfur in the gas stream at multiple locations of varying pressure and temperature with a goal to create their own sulfur deposition prediction model. However, the cost, time, safety issues, and complexity of doing so would be cumbersome to the point of complete impracticability.

In summary, what is needed, and what is lacking in current art, is a sulfur deposition prediction model developed for use by oil and gas production personnel. To create such a model, tailored for oilfield gas operations, three types of data are required:

1. The amount of sulfur dissolved in a gas where it enters gas handling facilities, which is a function of its composition, pressure, and temperature;
2. The amount of sulfur dissolved in the gas as a function of temperature reduction; and
3. The amount of sulfur dissolved in the gas as a function of pressure reduction.

It is the expressed intention of the present invention, by means of continuous gas flow capabilities, to generate, with accuracy and precision, these three data, which will provide the means for creating a sulfur deposition prediction model developed for use by oil and gas production personnel.

SUMMARY

The present invention relates to the evaluation of gas fields and facilities regarding the potential for sulfur deposits, and more specifically, relates to a continuous gas flow system and process for measuring the sulfur solubility of a gas of interest, such as a gas from a new exploratory field.

The present invention is directed to methods and systems for measuring the sulfur solubility of a test gas at a selected test temperature and pressure in a laboratory type apparatus. One exemplary method for determining the sulfur solubility of the gas of interest (the "test gas") includes the step of flowing the test gas into a first conduit that can be located at a first station of the system. The first conduit is packed with elemental sulfur, and is maintained at least at a first temperature that is sufficient to result in the uptake of elemental sulfur by the test gas as it flows through the first conduit. The uptake of elemental sulfur by the test gas is in excess of the natural equilibrium solubility level of elemental sulfur in the test gas at the test temperature.

The method further includes the step of introducing the test gas into a second conduit. The second conduit is in fluid communication with the first conduit and maintained at least at a second temperature sufficient to lower the temperature of the test gas to a temperature that is equal to the test temperature, such that the amount of elemental sulfur in the test gas is reduced to its natural equilibrium solubility level in the test gas at the test temperature. Subsequently, the saturated test gas flows into a third conduit that is in fluid communication with the second conduit. At least a portion of the third conduit is maintained at a third temperature sufficient to result in deposition of the elemental sulfur from the saturated test gas into a portion of the third conduit. The sulfur solubility of the test gas is calculated based on the amount of elemental sulfur deposited in the third conduit and the volume of the test gas that passes through the system in a given experimental run.

BRIEF DESCRIPTION OF THE DRAWING FIGURES

Further aspects of the present disclosure will be more readily appreciated upon review of the detailed description of its various embodiments, described below, when taken in conjunction with the accompanying drawings, of which.

DETAILED DESCRIPTION OF CERTAIN EMBODIMENTS

The present disclosure details systems and methods for determining sulfur solubility in a gas stream in a laboratory-type environment or other test site/experimental setting. While conventional laboratory methods utilize a closed system (i.e., no gas flow) where a known volume of gas is pressurized to a specific pressure inside an equilibrium cell or autoclave, the present systems and methods utilize a continuous gas flow system (i.e., continuous gas flow through the equipment). The use of a continuous gas flow allows the present invention to collect sufficient sulfur for accurate and precise measurement, whereas a closed or sealed vessel does not. More particularly, the ability to flow the gas continuously at a test pressure and a test temperature for long durations (e.g., hours, days, weeks) allows for very accurate analysis of the sulfur solubility of a gas, even for gases at low pressures and temperatures where sulfur uptake in the gas is expected to be extremely low. Another advantage of this invention is its ability to better simulate the conditions of an actual gas line in which gas naturally flows. Further, the present invention can assist in developing numerical computational models for the prediction of sulfur solubility and deposition of any gas under a wide range of parameters (e.g., gas composition, temperature, pressure).

The laboratory systems and methods of the present application can be used to measure the deposition and solubility of elemental sulfur (e.g., in parts per million [ppm] levels) for a particular gas stream. In one or more embodiments, a gas stream of interest enters a first conduit, where the gas stream is sufficiently charged with high levels of sulfur. The gas stream of interest may, for example, comprise a target gas from a new gas field or any other gas stream known by the operators to have sulfur-related issues. The gas stream containing high levels of elemental sulfur then flows to a second conduit where the test temperature is lower than that of the first conduit (but at same pressure). This drop in temperature in the second conduit causes excess sulfur from the first conduit to deposit. The gas that exits the second conduit is saturated with sulfur at the test temperature and at the test pressure. After exiting the second conduit, the sulfur-saturated gas stream flows into a third conduit, where the conditions are sufficient to cause the sulfur in the gas stream to condense and precipitate at a collection site. The weight of the deposited sulfur and the total volume of the test gas that passed through the system can then be determined in order to calculate the sulfur solubility of the gas stream.

The systems and methods of the present application allow for the determination of the solubility of elemental sulfur in both dry and wet gases at varying temperatures and pressures, including low temperatures and/or low pressure. In particular, the present systems and methods utilize a continuous gas flow system (i.e., continuous gas flow through the equipment). The use of a continuous gas flow allows the present invention to collect sufficient sulfur for accurate and precise measurement whereas conventional laboratory methods (closed or sealed vessel) do not.

More specifically, conventional laboratory methods utilize sealed (no continuous gas flow) pressure vessels of rather small size (typically a liter or less in volume). The environment to be tested is recreated inside of the pressure vessel. After some time, a small sample of gas from the vessel is removed and analyzed for the sulfur it contains. One problem with the conventional methods is that the amount of sulfur contained in these gases under their true natural equilibrium levels is incredibly small (e.g., low parts per million). As such, the amount of sulfur collected through these conventional methods is so small that it creates enormous analytical challenges to even detect the sulfur let alone determine the amount collected with confidence.

The system of the present application has the ability to achieve natural equilibrium levels of elemental sulfur in a gas at fixed levels of pressure, temperature, and gas composition. The system also has the capability of functioning with any gas composition typically found in oilfield environments (including those containing hydrogen sulfide), as well as other types of gas compositions.

Another advantage of this invention is its ability to better simulate the conditions of actual gas line equipment in which gas naturally flows. Yet another advantage of this system over prior art is that water-saturated gases streams can be used. More specifically, in at least one embodiment, the system can saturate the gas with water at a test pressure and test temperature. The primary source of elemental sulfur in gas compositions typically found in oilfield environments is from sulfur that naturally occurs in below ground formations that contain the oil and gas. Water is also normally present in the below ground formations that contain the oil and gas, and as such the gas produced from below ground formations is normally saturated with both water and sulfur. Water saturation in the gas can have a large influence on the solubility level of sulfur in the gas. Thus, the ability to determine sulfur solubility in both wet and dry gases is an improvement on the existing art. The referenced systems and methods for measuring the sulfur solubility in a gas stream in a laboratory-type environment are now described more fully with reference to the accompanying drawings, in which one or more illustrated embodiments and/or arrangements of the systems and methods are shown. The systems and methods are not limited in any way to the illustrated embodiments and/or arrangements as the illustrated embodiments and/or arrangements described below are merely exemplary of the systems and methods, which can be embodied in various forms, as appreciated by one skilled in the art. Therefore, it is to be understood that any structural and functional details disclosed herein are not to be interpreted as limiting the systems and methods, but rather are provided as a representative embodiment and/or arrangement for teaching one skilled in the art one or more ways to implement the systems and methods.

Figure 1:
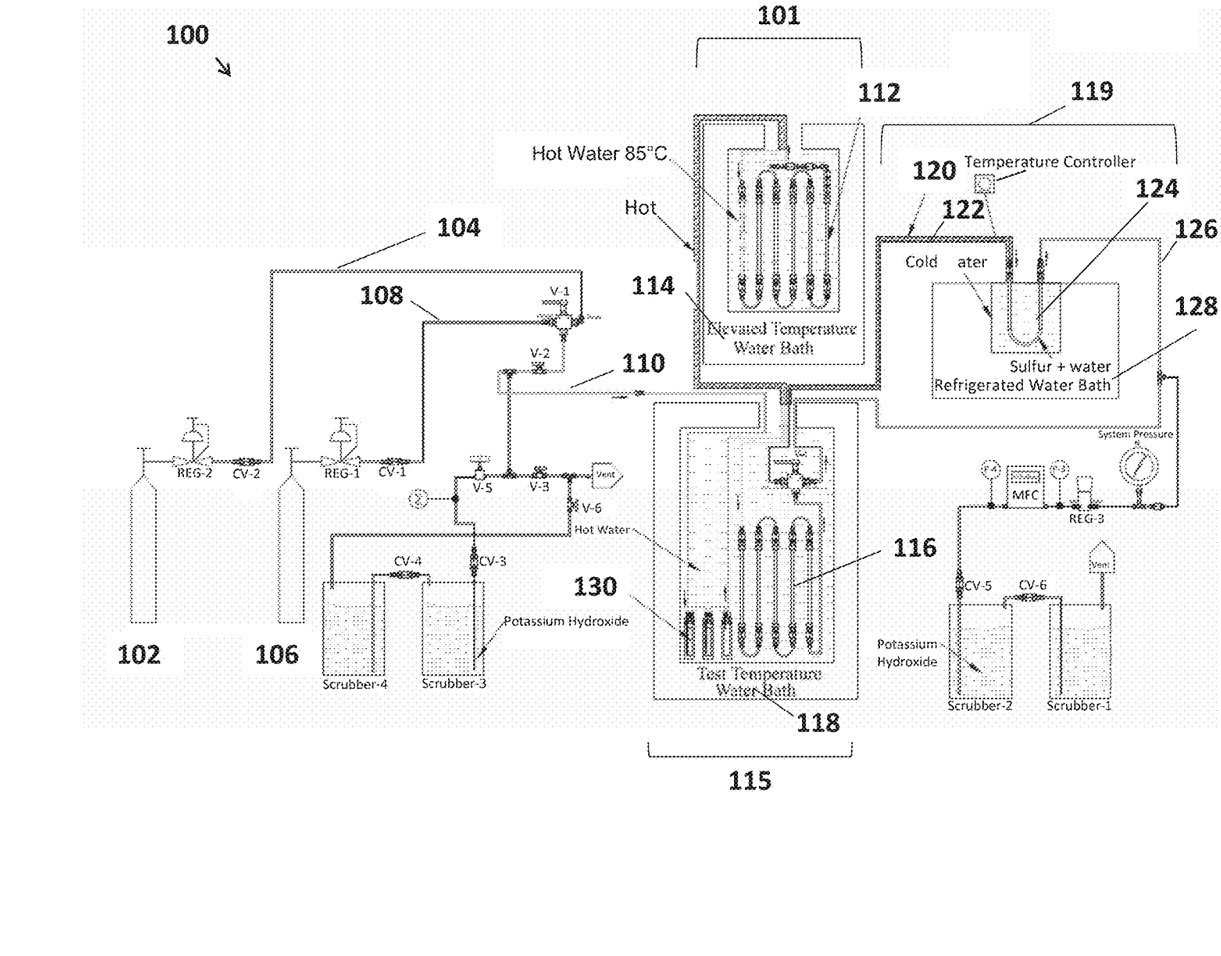
FIG. 1 is a schematic of a system for measuring sulfur solubility in a gas in accordance with one or more embodiments of the present application.

FIG. 1 illustrates an exemplary system 100 for determining the sulfur solubility of a selected (target) gas stream in a laboratory-type environment or other test/experimental setting. FIG. 1 also shows an exemplary flow scheme. The system 100 includes a gas source such as a vessel (e.g., container or tank) 102, which contains the test gas of interest (test gas) for the system 100. The test gas can comprise one or more of a variety of gases including, but not limited to, $CH_4$, $CO_2$, and $H_2S$ (or any combination thereof), or any other gas compositions for which sulfur deposition is a concern, such as any gas found in typical oil production environments or gas streams with anticipated sulfur (or other trace elements such as mercury) deposition problems, as well as similar gases in industries other than oil and gas.

In one or more embodiments, the flow rate of the fluids of system 100 is controlled by a flow control system that includes one or more digital mass flow meters, pressure regulators, valves, gauges, and/or pressure safety elements (e.g., rupture disks). While the flow control system of system 100 (see, FIG. 1) (as described in the Example section below) is configured in a particular way, any number of configurations for the valves, regulators, gauges and the like can be used for the flow control system in order to accomplish the specified flow rates of fluids within the system 100.

While the test gas of system 100 emulates the gas stream of actual gas line equipment or can be sampled from existing gas line equipment, it should be noted that the system 100 itself is designed to be remote and not directly connected to a gas line structure. As such, the system 100 is a laboratory (test) system that is separate and remote from a live gas-handling system.

Referring again to FIG. 1, the test gas flows from vessel 102 through a first fluid channel 104 (e.g., pipe, tube) to the rest of system 100. In one or more embodiments the system 100 can also include a nitrogen ($N_2$) gas vessel (tank or container) 106. In at least one embodiment, the $N_2$ gas in the vessel 106 can be pumped through second and third fluid conduits 108 and 110, respectively, to the rest of the system 100 to purge the system 100 of any oxygen prior to the initiation of a test run for a test gas of interest. However, in at least one implementation, the system can allow for oxygen to be introduced into the gas stream. As shown in the figures, the conduits described herein can include traditional equipment, such as valves, regulators, etc., to control the flow of both the nitrogen gas and the test gas. As shown the first and second conduits 104, 108 flow to a valve mechanism that is also connected to the third conduit 110 (e.g., a pipe or tube) that delivers the respective gas to the downstream test equipment of the system 100.

To begin the test run for a test gas, the test gas flows from vessel 102 through the first conduit 104 and the third conduit 110 and is delivered to a first station (section) 101 of system 100. The first station 101 of the system 100 is designed to charge the gas stream with high levels (not necessarily saturation levels) of elemental sulfur under select, prescribed conditions that promote such activity. The first station 101 of the system 100 includes a fourth conduit (the claimed first conduit) 112 that is in fluid communication with the third conduit 110. As a result, the fourth conduit 112 is packed with elemental sulfur and the conditions of the fourth conduit 112 are such that the test gas becomes charged with high levels of elemental sulfur prior to exiting the fourth conduit 112. In one or more implementations, the elemental sulfur in the fourth conduit 112 is in powder form and is disposed within the fourth conduit 112 along select portions (lengths) of the fourth conduit 112.

During its flow through fourth conduit 112, the test gas "picks up" the elemental sulfur such that the test gas is sufficiently charged with high levels of elemental sulfur (this results from the test gas flowing through the elemental sulfur). The level of elemental sulfur pick up of the test gas is a function of the particular test gas composition as well as the pressure within and the temperature of the fourth conduit 112, as well as the residency time of the test gas inside the fourth conduit 112. Residency time must be long enough to ensure sufficiently high level of sulfur uptake by the gas stream before it enters the second water bath. In one or more implementations, the test gas, when exiting the fourth conduit 112, contains an amount of elemental sulfur that exceeds the natural equilibrium solubility level of elemental sulfur in the test gas at the lower test temperature (test temperature) that exists in conduit 116. Adequate residency time in the fourth conduit 112 can be critical to providing the most accurate measurements. As such, in one or more embodiments, the gas flow rate of the test gas can be set to a low value to ensure adequate residence time in the fourth conduit 112. For instance, in one or more embodiments the gas flow rate of the test gas into the fourth conduit 112 is about 50 ml/min. The gas flow rate of the test gas into and through the fourth conduit 112 can also be affected by the physical structure of the fourth conduit 112 (e.g., the number of loops and the dimensions of the fourth conduit 112).

In one or more implementations, the temperature of the fourth conduit 112 is elevated such that the temperature of the test gas in the fourth conduit 112 increases and becomes sufficient to result in sufficiently high levels of sulfur uptake by the test gas. The temperature of the fourth conduit 112 required for sufficiently high levels of sulfur pickup can vary depending on, for example, the components of the test gas and the dimensions of the fourth conduit 112. In one or more implementations, the temperature of fourth conduit 112 is less than or equal to 95° C. In one or more embodiments, the temperature of the fourth conduit 112 can be predetermined based on the known components of the test gas and the dimensions of the fourth conduit 112. It will be appreciated that other factors can be considered in selecting the target temperature for the fourth conduit 112.

The temperature of the fourth conduit 112 can be controlled in various ways known to those having ordinary skill in the art. In at least one embodiment (as shown in FIG. 1), the fourth conduit 112 can be exposed to a heating medium and in particular, the fourth conduit 112 can be located within a water bath 114. In this embodiment, the temperature of the water bath 114 can be manipulated in order to change the temperature of the fourth conduit 112 and, consequently, the temperature of the test gas that flows through the fourth conduit 112. The fourth conduit 112 can thus be submerged or otherwise in contact with a medium, such as water in the bath 114.

In at least one embodiment, the fourth conduit 112 can be a single pipe or tube. In one or more embodiments, the fourth conduit 112 can also be a group of interconnected pipes or tubes arranged in series. For example, as shown in FIG. 1, the fourth conduit 112 can be a series of interconnected tubes arranged in a serpentine manner for increasing the surface area and exposure of the gas to the medium (e.g., water) that surrounds and heats the fourth conduit 112. In one or more embodiments, the series of interconnected tubes have a large diameter (e.g., 0.5 inches). The large diameter of the interconnected tubes allows for longer contact time between the test gas and the sulfur powder, which ensures that the test gas is sufficiently charged with high levels of elemental sulfur prior to exiting the fourth conduit 112. In one or more embodiments, the residency time of the test gas in the fourth conduit 112 is at least 2 hours. A relatively long residency time coupled with the elevated temperature allows the test gas, when exiting the fourth conduit 112, to contain an amount of elemental sulfur that exceeds the natural equilibrium solubility level of elemental sulfur in the test gas at the lower test temperature that exists in conduit 116. It should also be noted that the vessels and/or conduits of the present system can be made of metals or a mixture of metals as is known in the art. In one or more embodiments, the vessels and/or conduits of the present system can be made of one or more corrosion resistant alloys.

Following sufficiently high levels of sulfur uptake by the test gas in the first station or stage 101 of the present invention, the now sulfur-charged test gas flows from the first station or stage to a second station or stage 115 of the system 100. More specifically, the sulfur-charged test gas flows from the fourth conduit 112 associated with the first station 101 to a fifth conduit (the claimed second conduit) 116 that is associated with the second station/stage 115. The second station 115 is configured to decrease the temperature of the test gas to a prescribed temperature (range). In particular, the conditions of the second station 115 are such that the test gas, in the fifth conduit 116, is lowered to a temperature that simulates the temperature the test gas would be in a system for processing or transporting gas streams where sulfur pick up is anticipated (i.e., the test temperature). In other words, the temperature of the fifth conduit 116 (in the second station) alters the temperature of the test gas to a temperature substantially equivalent to a selected test temperature prior to exiting the fifth conduit 116. The test temperature can vary based on, for example, the components of the test gas and the dimensions of the fifth conduit 116. In one or more embodiments, the test temperature is 10-15° C. lower than the temperature of the fourth conduit 112.

Further, the gas flow conditions in the second stage 115 are carefully tailored in that the temperature of the fifth conduit 116 and the pressure of the gas flowing therein are predetermined (i.e., the test temperature and test pressure) based on the industrial process conditions for which the operator is trying to determine sulfur solubility. As discussed above, the test gas enters the fifth conduit 116 at an elevated temperature and it contains sulfur in excess of the solubility limit for the gas at the test temperature of the fifth conduit 116. As such, when the test gas enters the fifth conduit 116, the conditions (e.g., the test temperature and test pressure) are such that the test gas deposits the excess sulfur on the walls of the fifth conduit 116. The residency time of the test gas in fifth conduit 116 is sufficient to ensure that the test gas reaches its natural equilibrium solubility level for sulfur at the particular test temperature and test pressure. As such, as the test gas exits fifth conduit 116, it is saturated with sulfur at the test temperature and test pressure.

As with the fourth conduit 112, the temperature of the fifth conduit 116 can be controlled in various ways known to those having ordinary skill in the art. In at least one embodiment (as shown in FIG. 1), the fifth conduit 116 can be disposed within a cooling medium, in this case, a water bath 118. In this embodiment, the temperature of the water bath 118 can be manipulated in order to change (e.g., lower) the temperature of the fifth conduit 116 and, consequently, the temperature of the sulfur-saturated test gas flowing therein.

The residency time of the sulfur-saturated test gas inside the fifth conduit 116 must be long enough to ensure that the test gas exits the fifth conduit 116 at the desired temperature (i.e., substantially equal to the test temperature). Generally, the residency time of the test gas in fifth conduit 116 is shorter than the residency time of the test gas in the fourth conduit 112. As such, in one or more embodiments, the gas flow rate of the sulfur-saturated test gas into the fifth conduit 116 can be altered (e.g., via a mass flow controller) to ensure adequate residence time in fifth conduit 116. The gas flow rate of the test gas is generally calculated and set at the beginning of a test run. The gas flow rate of the sulfur-saturated test gas in the fifth conduit 116 can also be affected by the dimensions of the fifth conduit 116. For example, the fifth conduit 116 can be a single coiled tube having a ⅛ inch outside diameter, or the like. In one or more embodiments, the fifth conduit 116 can also be group of interconnected pipes or tubes arranged in series. As shown in FIG. 1, for example, the fifth conduit 116 can be a series of interconnected tubes or pipes arranged in a serpentine manner to increase the surface area and allow the gas flowing therein to be subjected to the cooling medium.

After the temperature of the sulfur-saturated test gas is lowered in the fifth conduit 116, the sulfur-saturated test gas flows into a third station or stage 119 of the system 100. As described herein, the third station/stage 119 is one in which elemental sulfur is collected as precipitate from the test gas in a controlled manner. The third station/stage 119 includes a sixth conduit (the claimed third conduit) 120 that is fluid connected to the fifth conduit 116 of the second station 115. As described herein, the gas flows within the sixth conduit 120 and is subjected to conditions that cause the deposition of the elemental sulfur from the test gas in a manner that allows the elemental sulfur to be carefully collected, measured and analyzed.

In one or more implementations, all of the sulfur in the test gas is deposited in the sixth conduit 120 in a collection zone.

In one or more embodiments (as shown in FIG. 1), the sixth conduit 120 comprises three sections, namely, an inflow section 122, a trap section 124, and an outflow section 126. In one or more implementations, the inflow section 122 is a continuously heated tube or pipe fluidly connected to the conduit 116. The conditions of the inflow section 122 (e.g., temperature, pressure) ensure that the temperature of the sulfur-saturated test gas (from fifth conduit 116) remains high enough to avoid any deposition of the elemental sulfur within the inflow section 122.

With continued reference to FIG. 1, the sulfur-saturated test gas flows from the inflow section 122 to the trap section 124. The conditions of the trap section 124 are such that the sulfur-saturated test gas precipitates (deposits) the sulfur in the trap section 124. Specifically, in one or more embodiments, upon entering the trap section 124, the sulfur-saturated test gas mixture is "quenched" (rapidly cooled) to a very low temperature resulting in the immediate condensation and deposition of the total quantity of sulfur dissolved in the saturated test gas. After the deposition of the elemental sulfur in the trap section 124, the weight of the deposited sulfur is determined using conventional analytical techniques and equipment.

It should be noted that, in one embodiment, the trap section 124 acts on the temperature of the test gas flowing therein but not the pressure of the gas. It is desirable to limit or prevent any change in the pressure of the gas since a system that acts on the pressure of the test gas would result in precipitation at the location of a pressure-reducing device and thus an increased potential for inaccurate measurements. In one or more embodiments (as shown in FIG. 1), the trap section 124 can be a U-shaped tube. The U-shaped tube allows for the deposited sulfur to gather at the bottom of the "U," which allows for easier collection and subsequent measurement of the deposited sulfur since the precipitated gas will not flow downstream of the U-shaped section. The U-shaped tube also ensures that deposited sulfur won't be pushed by the gas flow and lifted to a scrubber tank located downstream, which would affect the measured solubility values. In at least one embodiment, the trap section 124 can be V-shaped or have another configuration that results in the precipitated sulfur collecting in a zone due to gravitational forces.

As with the other sections of system 100, the temperature of the trap section 124 can be controlled in various ways. For example, in at least one embodiment (as shown in FIG. 1), the trap section 124 can be located within a cooling/quench medium, in that case a water bath 128. In this embodiment, the temperature of the water bath 128 can be manipulated in order to quickly lower the temperature of the sulfur-saturate test gas upon entrance into trap section 124. In addition, it will be appreciated that the trap section 124 could be disposed within or otherwise in contact with other cooling medium, such as a gas that has a cooled temperature.

As mentioned above, following the deposition of the sulfur in trap section 124, the weight of the deposited sulfur is determined. For example, the trap section 124 can be removed from the other sections 122, 126 and then the collected sulfur will be dissolved in a known organic solvent and analytically analyzed, using conventional analytical technique, for its weight. In at least one embodiment, connectors, such as quick release connectors, can be used to connect the trap section 124 to the other sections 122, 126. Additionally, the now unsaturated test gas exits the trap section 124 and enters the outflow section 126, where the total volume of the test gas mixture that has passed through the system 100 during the test duration is measured using conventional equipment (e.g., flow meter, mass flow controller). The weight of the deposited sulfur and the total volume of the test gas mixture that passed through the system 100 during the test run are then used to determine the sulfur solubility of the test gas mixture. The sulfur solubility can be calculated either in Normal conditions or Standard conditions of temperature and pressure, as shown in further details in the Examples section below.

The above described system 100 can be run at various temperatures and/or pressures depending on various factors related to the system, including the components of the test gas, and the shape and dimensions of the different portions of the system. In an exemplary embodiment, the system 100 is run at a pressure of between about 100 psia and about 1000 psia, and is constant through the system. The temperature in the first station and second station can range from approximately 5° C. to 95° C., while the temperature of the cooling/quench medium (e.g., water bath 128) is approximately 0.0° C. or lower.

The above described methods and systems can utilize a dry gas as the test gas. In one or more alternative embodiments a wet gas can also be used as the test gas. In an embodiment in which the test gas is a wet gas, the test gas is first saturated with water prior to being saturated with sulfur. For example, in at least one embodiment, the test gas first flows from gas vessel 102, through conduits 104 and 110, and into vessel 130. In vessel 130, the test gas is saturated with water. Following water saturation in vessel 130, the now "wet" test gas flows into conduit 112, to uptake sufficiently high levels of elemental sulfur. The remainder of the process for the water saturated gas continues in the same fashion as described in the above description of the method. In one or more embodiments, the vessel 130 is a stand-alone vessel. In at least one embodiment, as shown in FIG. 1, the vessel 130 is located within the test temperature water bath 118.

EXAMPLES

The following examples are provided to better illustrate embodiments of the present invention, but they should not be construed as limiting the scope of the present invention.

In these examples, five test runs were conducted, and the test gas used for each test run was methane ($CH_4$). As shown in Table 1 (below), the test temperature varied between 30° C. and 70° C. and the test pressure varied between 300 psia and 1000 psia for the five test runs. The high-temperature water bath (first station) was set to 85° C., while the test temperature water bath (second station) was set to the desired test temperature (see Table 1 for the test temperature of each run). The pressure of the system was also set to the desired test pressure (see Table 1 for the test pressure of each run).

Each test run was conducted using the following protocol (with reference to FIG. 1):

First the tube heating (heat controller) was turned on. Next, the three water baths were evaluated to ensure that the water level in all three water baths was correct. The high-temperature gas saturation water bath was turned on and set for 85° C. The test temperature water bath was turned on and set to the desired saturation temperature for the test run. The cold water bath circulation and cooling switches were turned on. The water baths were left for several hours to equilibrate to their correct set-point temperatures. The main valve of the test gas cylinder was closed and the test gas cylinder regulator (REG-2) was adjusted to its lowest pressure setting. V-1 was then opened test gas position (valve handle points to the label indicating the valve position).

Next, V-2 was opened, V-4 was opened to gas bypass, V-3 was closed, and V-5 was closed. The main valve of the test gas cylinder was then opened. The test gas cylinder regulator (REG-2) was then slowly adjusted until the pressure gauge indicated the exact desired test pressure. Next, the pressure indicated on the system pressure gauge (P-2) was verified to ensure that it equaled the desired test gas pressure. The regulator (REG-3) was then adjusted between 30 and 60 psig, but not to exceed the maximum inlet pressure of the mass flow controller (MFC-1). In the present case, the digital mass flow meter was operated in the range 0-200 mL/min (equivalent $N_2$) with a maximum inlet pressure of 150 psig.

Next the value of the Gas Correction Factor (GCF) corresponding to the specific gas blend was adjusted. The value of the desired flow rate (mL/min) and the frequency of data saving were also adjusted. The test gas at the desired flow rate and at the desired pressure then flowed through the gas bypass portion of the system, and it was verified by the operator that all three water baths had reached their correct set-point temperatures.

V-4 was then opened to the position for collecting sulfur (valve located in the Test temperature bath). The date and time at which sulfur collection started in the sample collection tube (U-tube) was then recorded along with the test gas composition, the test gas pressure, the test gas flow rate, and the temperatures of the three water baths.

To terminate sulfur collection, V-4 was opened to the gas bypass position (valve located in the test temperature water bath). The date and time at which sulfur collection stops in the sample collection tube was then recorded. After sulfur collection ended, the tube heat was turned off, and the elevated temperature and test temperature water baths were turned off. Next, the main valve of the test gas cylinder was closed, followed by the closure of V-2, V-5, and V-6. V-3 was then slowly opened release the high pressure gas in the system. The pressure gauges were observed until all pressure gauges show zero pressure.

At the end of each test run, the sulfur solubility of the test gas was calculated using the following equation:

$$S_{NC}[mg/Nm^3] = \frac{m[mg]}{V[Nm^3]} = \frac{m}{60 \times 24 \times 10^{-6} \times Q_v \Delta t} \times \frac{298.15}{273.15}$$

where $S_{NC}$ is the sulfur solubility at Normal conditions (0° C. [273.15 K] and 1 atm), m[mg] is measured weight of deposited sulfur, $Q_v$ [ml/mn] is the flow rate of gas controlled via the mass flowmeter (Note that the flowmeter controls the flow of gas downstream the flowmeter, which is at 25° C. [298.15 K] and ambient pressure) and $\Delta t$ [days] is the total test duration. For the solubility in Standard conditions (60° F. [288.7 K] and 1 atm), conversion factors are introduced as follows:

$$S_{NC}[lb/MMSCf] = S_{NC}[mg/Nm^3] \times \frac{2.204}{37.326}$$

The results for each test run are shown in Table 1.

TABLE 1

Sulfur Solubility of Experiments 1-5.

| Exp. # | Gas | Test Temp. (° C.) | Test Pressure (psia) | Sulfur weight (mg) | Total gas volume measured a t25° C. and 1 atm ($m^3$) | Calculated Solubility lb/MMScf | Calculated solubility in ppmw |
|---|---|---|---|---|---|---|---|
| 1 | $CH_4$ | 70 | 1000 | 0.756 | 0.527 | 0.0925 | 2.186 |
| 2 | $CH_4$ | 70 | 500 | 0.41 | 0.506 | 0.0522 | 1.233 |
| 3 | $CH_4$ | 70 | 300 | 0.4 | 0.514 | 0.0502 | 1.185 |
| 4 | $CH_4$ | 45 | 300 | 0.09 | 0.504 | 0.0115 | 0.272 |
| 5 | $CH_4$ | 30 | 300 | 0.04 | 0.504 | 0.005 | 0.106 |

The terminology used in the above description is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "including," "comprising," "having," "containing," "involving," and variations thereof herein, when used in this specification, specify the presence of stated features, integers, steps, operations, elements, and/or components, but do not preclude the presence or addition of one or more other features, integers, steps, operations, elements, components, and/or groups thereof.

It should be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Also, the phraseology and terminology used herein is for the purpose of description and should not be regarded as limiting.

While the present system is described as containing multiple stations, it will be appreciated that all of the stations and equipment can be contained in a single housing or the like (i.e., under the same footprint). The invention is discussed in terms of stations for purposes of illustration only and to discuss the different operations that occur in separate parts of the system. In addition, two or more of the conduits discussed herein can be physically a single tube and the discussion of different conduits is merely for exemplary purposes to relate the portion of the conduit to one of the stations discussed herein.

While the present invention has been described above using specific embodiments, there are many variations and modifications that will be apparent to those having ordinary skill in the art. As such, the described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A method for measuring the sulfur solubility of a test gas at a test temperature and test pressure in a laboratory apparatus, comprising:
    saturating the test gas with water;
    flowing the test gas into a first conduit, wherein the first conduit is packed with elemental sulfur, and is maintained at least at a first temperature that is sufficient to result in the uptake of elemental sulfur by the test gas in excess of the natural equilibrium solubility level of elemental sulfur in the test gas at the test temperature;
    introducing the test gas containing elemental sulfur into a second conduit, the second conduit being in fluid communication with the first conduit and maintained at least at a second temperature sufficient to lower the temperature of the test gas to a temperature that is equal to the test temperature, whereby the amount of elemental sulfur in the test gas is reduced to its natural equilibrium solubility level in the test gas at the test temperature;
    flowing the test gas into a third conduit that is in fluid communication with the second conduit, wherein at least a portion of the third conduit is maintained at a third temperature sufficient to result in deposition of the elemental sulfur from the test gas into a portion of the third conduit; and
    calculating the sulfur solubility of the test gas based on the amount of elemental sulfur deposited in the third conduit.

2. The method of claim 1, wherein the test gas comprises $CH_4$.

3. The method of claim 2, wherein the test gas further comprises $CO_2$ and $H_2S$.

4. The method of claim 1, wherein the step of calculating the sulfur solubility comprises:
    weighing the sulfur deposited in the third conduit for a select run time; and
    measuring the volume of the test gas that passes through the third conduit during the select run time.

5. The method of claim 1, wherein the third conduit comprises a U-shaped tube.

6. The method of claim 1, wherein the first temperature is a maximum of 95° C.

7. The method of claim 1, wherein the test temperature is 10-15° C. lower than the first temperature.

8. The method of claim 1, wherein the third temperature is 0° C.

9. The method of claim 1, wherein the laboratory apparatus is free of direct contact with gas-handling equipment that contains the test gas.

10. A system for measuring the sulfur solubility of a test gas at a test temperature, comprising:
    a source of the test gas;
    a first station in fluid communication with the source of test gas, the first station comprising a first conduit packed with elemental sulfur, wherein the first conduit is maintained at conditions sufficient to result in the uptake of elemental sulfur by the test gas as the test gas flows through the first conduit, the uptake of elemental sulfur being in excess of the natural equilibrium solubility level of the elemental sulfur in the test gas at the test temperature;
    a second station comprising a second conduit in fluid communication with the first conduit, wherein the second conduit is maintained at conditions sufficient to lower the temperature of the test gas to the test temperature, whereby the amount of elemental sulfur in the test gas is reduced to its natural equilibrium solubility level in the test gas at the test temperature; and
    a third station comprising a third conduit in fluid communication with the second conduit, wherein the third conduit is maintained at conditions that cause deposition of the elemental sulfur from the test gas, the third conduit being configured such that the deposited elemental sulfur can be collected and weighed to calculate the sulfur solubility of the test gas based on a measured flow rate of the test gas through the system; and
    a fourth conduit in fluid communication with the source of test gas and upstream of the first conduit, wherein the conditions of the fourth conduit are sufficient to saturate the test gas with water as the test gas flows through the fourth conduit prior to entering the first station.

11. The system of claim 10, wherein the system is a continuous flow loop system.

12. The system of claim 10, wherein the first station includes a first medium for elevating a temperature of the test gas flowing through the first conduit; the second station includes a second medium for decreasing the temperature of the test gas to the test temperature and the third station includes a third medium for quenching the sulfur-saturated test gas by decreasing the temperature thereof.

13. The system of claim 12, wherein the first, second, and third mediums comprise water contained within respective first, second and third baths, the first, second and third conduits being surrounded by the first, second and third mediums, respectively.

14. The system of claim 10, wherein the fourth conduit is located within the second station.

15. The system of claim 10, wherein the first conduit comprises a plurality of first tubes arranged in series and contained within a first medium that is heated to elevate the temperature of the test gas.

16. The system of claim 15, wherein the plurality of first tubes are configured in a serpentine arrangement.

17. The system of claim 10, wherein the second conduit comprises a plurality of second tubes arranged in series and contained within a second medium that is cooled to decrease the temperature of the test gas to the test temperature.

18. The system of claim 17, wherein the plurality of second tubes are configured in a serpentine arrangement.

19. The system of claim 10, wherein the third conduit comprises an inflow section for maintaining the test gas at the test temperature, a trap section for collecting the deposited sulfur, and an outflow section downstream of the trap section for carrying the test gas from the third station, wherein the inflow section and the outflow section are elevated above the trap section.

20. The system of claim 19, wherein the trap section comprises a U-shaped tube.

21. The system of claim 10, further including a flow meter for calculating a flow rate of the test gas through the system, thereby allowing a total volume of test gas to be calculated for a given experimental run.

22. The system of claim 10, further including a pressure regulator for maintaining a pressure of the test gas within a prescribed range as the test gas flows through each of the first, second and third stations.

23. The system of claim 10, further including a temperature controller for monitoring the temperature of the test gas and adjusting the temperature of the test gas.

24. The system of claim 10, wherein the source of test gas comprises a tank of sour gas collected from a gas field of interest.

* * * * *